(12) United States Patent
Platzek et al.

(10) Patent No.: US 7,385,054 B2
(45) Date of Patent: Jun. 10, 2008

(54) TRIMERIC, MACROCYCLICALLY SUBSTITUTED HALO-BENZENE DERIVATIVES

(75) Inventors: Johannes Platzek, Berlin (DE); Heiko Schirmer, Berlin (DE); Hanns-Joachim Weinmann, Berlin (DE); Jose Luis Martin, Madrid (ES); Juan R. Harto, Madrid (ES)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 11/272,008

(22) Filed: Nov. 14, 2005
(Under 37 CFR 1.47)

(65) Prior Publication Data

US 2006/0154989 A1    Jul. 13, 2006

Related U.S. Application Data

(63) Continuation of application No. 11/122,248, filed on May 5, 2005.

(60) Provisional application No. 60/574,713, filed on May 27, 2004.

(30) Foreign Application Priority Data

May 5, 2004    (DE) .................. 10 2004 023 093

(51) Int. Cl.
*C07D 295/02*    (2006.01)
*C07D 295/023*    (2006.01)
*C07D 249/02*    (2006.01)

(52) U.S. Cl. .................. 540/474; 540/450; 540/465; 540/470

(58) Field of Classification Search .............. None
See application file for complete search history.

(56) References Cited

U.S. PATENT DOCUMENTS 5,403,576 A *    4/1995    Lin et al. .................. 424/9.34
5,660,814 A       8/1997    Uggeri et al.
2004/0265236 A1   12/2004   Schirmer et al.

FOREIGN PATENT DOCUMENTS

WO    WO 2004/074267 A    9/2004

OTHER PUBLICATIONS

A Albrecht et al. "The british Journal of Radiology", 73, (2000), p. 878-882.*

* cited by examiner

*Primary Examiner*—Yvonne Eyler
*Assistant Examiner*—Yevgeny Valenrod
(74) *Attorney, Agent, or Firm*—Millen, White, Zelano & Branigan, P.C.

(57) ABSTRACT

The metal complexes of general formula I

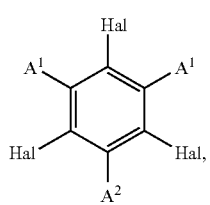

(I)

in which Hal stands for bromine or iodine, and $A^1$ and $A^2$ have different meanings, are suitable as contrast media.

20 Claims, No Drawings

TRIMERIC, MACROCYCLICALLY SUBSTITUTED HALO-BENZENE DERIVATIVES

This application is a continuation of U.S. patent application Ser. No. 11/122,248, filed May 5, 2005, which claims the benefit of U.S. Application Ser. No. 60/574,713 filed on May 27, 2004, both of which are fully incorporated by reference herein.

The invention relates to the subjects that are characterized in the claims: new trimeric, macrocyclically substituted tri-iodine and tribromobenzene derivatives, their production and use as contrast media in x-ray diagnosis and MRT diagnosis.

During the last decade, impressive advances were achieved in imaging diagnosis. The imaging techniques, such as DAS, CT and MRT, have developed into standard and indispensable tools in diagnosis and interventional radiology and now offer a spatial resolution of less than 1 mm. In addition, the possible applications of these techniques are increased decisively by the use of contrast media. This now wide distribution and acceptance of the contrast media in x-ray diagnosis can be attributed to the introduction of non-ionic monomeric tri-iodoaromatic compounds in the 1980's, as well as the isoosmolar dimeric iodoaromatic compounds that were introduced in the 1990's. By these two compound classes, the frequency of contrast medium-induced side effects was reduced to 2-4% (Bush, W. H., Swanson, D. P.: Acute Reactions to Intravascular Contrast Media: Types, Risk Factors, Recognition and Specific Treatment. AJR 157, 1153-1161, 1991. Rydberg, J., Charles, J., Aspelin, P.: Frequency of Late Allergy-Like Adverse Reactions Following Injection of Intravascular Non-Ionic Contrast Media. Acta Radiológica 39, 219-222, 1998). The use of contrast media in connection with modern imaging techniques now extends from the detection of tumors, for high-resolution vascular visualization, to the quantitative determination of physiological factors such as permeability or perfusion of organs. The concentration of the x-ray contrast medium (here, the iodine atom) is decisive for the contrast and the detection sensitivity. Despite further development of the technology, it was not possible to reduce the concentration or the dose to be administered that is necessary for a medical diagnosis. Thus, in a standard CT study, 100 g of substance or more is injected per patient.

Although the compatibility of the x-ray contrast media has been improved by the introduction of non-ionic triiodobenzenes, the number of side effects is still always high. Because of very high study numbers of several million per year in x-ray diagnosis, ten thousand patients are thus affected. These contrast medium-induced side effects extend from slight reactions such as nausea, dizziness, vomiting, and hives up to severe reactions such as bronchial spasms, or renal failure up to reactions such as shock or even death. Fortunately, these severe cases are very rare and are observed at a frequency of only 1/200,000 (Morcos, S. K., Thomsen, H. S.: Adverse Reactions to Iodinated Contrast Media. Eur Radiol 11, 1267-1275, 2001).

The frequency of these side effects, which are also observed as pseudoallergic contrast medium-induced side effects, is, however, increased by about a factor of 3 in atopic patients and by a factor of 5 in patients with a previous history of contrast medium-induced side effects. Asthma increases the risk of severe contrast medium-induced side effects by a factor of 6 in non-ionic contrast media (Thomsen, H. S., Morcos, S. K.: Radiographic Contrast Media. BJU 86 (Suppl1), 1-10, 2000. Thomsen, H. S., Dorph, S.: High-Osmolar and Low-Osmolar Contrast Media. An Update on Frequency of Adverse Drug Reactions. Acta Radiol 34, 205-209, 1993. Katayarna, H., Yamaguchi, K., Kozuka, T., Takashima, T., Seez, P., Matsuura, K.: Adverse Reactions to Ionic and Non-Ionic Contrast Media. Radiology 175, 621-628, 1990. Thomsen, H. S., Bush, Jr., W. H.: Adverse Effects on Contrast Media. Incidence, Prevention and Management. Drug Safety 19: 313-324, 1998). In these situations, the examiners for x-ray diagnosis in recent years most frequently use non-iodine-containing Gd-chelates instead of the standard tri-iodoaromatic compounds in computer topography but also in interventional radiology as well as DSA (Gierada, D. S., Bae, K. T.: Gadolinium as CT Contrast Agent: Assessment in a Porcine Model. Radiology 210, 829-834, 1999. Spinosa, D. J., Matsumoto, A. H., Hagspiel, K. D., Angle, J. F., Hartwell, G. D.: Gadolinium-Based Contrast Agents in Angiography and Interventional Radiology. AJR 173; 1403-1409, 1999. Spinosa, D. J., Kaufmann, J. A., Hartwell, G. D.: Gadolinium Chelates in Angiography and Interventional Radiology: A Useful Alternative to Iodinated Contrast Media for Angiography. Radiology 223, 319-325, 2002). This is, on the one hand, substantiated by the very good compatibility of the metal chelates that are used in MRT, but also by the known fact that lanthanides are also x-ray-opaque. In comparison to iodine, gadolinium and other lanthanides show a greater absorption than iodine especially at higher voltages/energies of the x-ray radiation, such that, in principle, they are suitable as opacifying elements for x-ray diagnosis (Schmitz, S., Wagner, S., Schuhmann-Giampieri, G., Wolf, K. J.: Evaluation of Gadobutrol in a Rabbit Model as a New Lanthanide Contrast Agent for Computer Tomography. Invest. Radiol. 30(11): 644-649, 1995).

The above-mentioned Gd-containing chelate compounds originally used in the MRT are also readily water-soluble and are distinguished by an excellent compatibility. Compared to the iodine-containing/non-ionic contrast media, the rate of light pseudoallergenic reactions is greatly reduced, and the rate of fatal reactions is extremely rare and is indicated with 1/1,000,000 (Runge, V. M.: Safety of Approved MR Contrast Media for Intravenous Injection. J. Magn Reson Imaging 12, 205-213, 2000). In contrast to other contrast medium-induced side effects, such as, e.g., the renal compatibility, pseudoallergic reactions are more likely independent of the administered dose. Also, the smallest dosages can accordingly already trigger a pseudoallergic reaction.

Desired are substances that combine the advantages of the two chemically entirely different classes of compounds.

The extraordinarily high hydrophilia of the metal chelates suggests a low incompatibility rate. Iodoaromatic compounds have a higher lipophilia by a factor of 100-200 (larger distribution coefficient between butanol/water) than metal chelates.

Based on the low substance concentration and the low specific proportion of the imaging metal in the entire molecule, the previously known metal chelates for x-ray diagnosis are not optimal (Albrecht, T., Dawson, P.: Gadolinium-DTPA as X-Ray Contrast Medium in Clinical Studies. BJR 73, 878-882, 2000). More recent attempts to solve this problem describe the production of metal complex conjugates, in which triiodoaromatic compounds are covalently bonded to an open-chain or macrocyclic metal complex (U.S. Pat. Nos. 5,324,503, 5,403,576, WO 93/16375, WO 00/75141, WO 97/01359, WO 00/71526, especially the U.S. Pat. No. 5,660, 814). Because of their low hydrophilia and high viscosity, the latter cannot be administered in adequate concentration and reasonable volumes, however.

In comparison to the compounds according to the invention, compound 3 from Example 3 and compound 4 from Example 4, disclosed in the closest prior art from U.S. Pat. No. 5,660,814, are 1) ionic and thus have an osmolality that is higher by a factor of 2 in comparison to the neutral compounds according to the invention, which is especially negative at high doses, 2) the latter are significantly more lipophilic than the compounds according to the invention (Note in column 5/line 29 of U.S. Pat. No. 5,660,814, the compounds from the prior art can be used as liver contrast media),
3) substances 3 and 4 of U.S. Pat. No. 5,660,814 are significantly more toxic than the compounds according to the invention (see $LD_{50}$ as well as distribution coefficient) and
4) the relaxivity for the MR imaging is thus lower.

The purpose is to produce compounds that have an adequate hydrophilia—comparable to that of Gd-chelates—and in addition to exhibit a high concentration of opacifying elements. Values that are significantly higher than those in metal chelates, which are approximately 25% (g/g), were desirable. In addition, at a higher concentration, a very good water solubility must be provided. In addition to their good pharmacological properties, the highly concentrated solutions must also indicate a practical viscosity and a low osmotic pressure.

This object is achieved by this invention.

The metal complexes of general formula I according to the invention

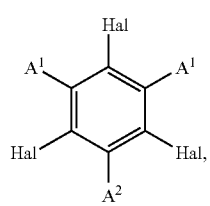
(I)

in which
Hal stands for bromine or iodine,
$A^1$ stands for the radical

—CONR$^1$—(CH$_2$)$_n$—NR$^2$—(CO—CHZ$^1$—NH)$_m$—CO—CHZ$^2$—K, $A^2$ stands for the radical —NR$^1$—CO—CHZ$^2$—K,
in which $R^1$ and $R^2$, independently of one another, are a hydrogen atom, a $C_1$-$C_2$-alkyl group or a monohydroxy-$C_1$-$C_2$-alkyl group,
$Z^1$ and $Z^2$, independently of one another, are a hydrogen atom or a methyl group,
n is the numbers 2-4,
m is the number 0 or 1, and
K stands for a macro cyclic compound of formula $I_A$

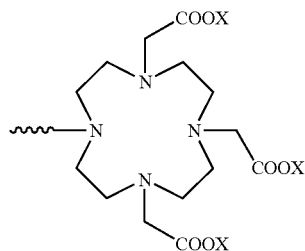
($I_A$)

with X in the meaning of a hydrogen atom or a metal ion equivalent of atomic numbers 20-29, 39, 42, 44 or 57-83, provided that at least two X stand for metal ion equivalents and optionally present free carboxy groups optionally are present as salts of organic and/or inorganic bases or amino acids or amino acid amides, show a very good solubility and a distribution coefficient that is comparable to that of Gd-chelates. In addition, the new compounds have a high specific content of opacifying elements, a low viscosity and osmolality and thus good tolerance/compatibility, so that they are extremely well suited as contrast media for x-ray and MR imaging.

Hal preferably stands for iodine, $R^1$ and $R^2$ stand for hydrogen and the methyl group, m stands for the number 0, and n stands for the number 2.

Radicals $A^1$ that are mentioned by way of example are:

—CONH(CH$_2$)$_{2,3}$NHCOCH$_2$NHCOCH(CH$_3$)—K,

—CONH(CH$_2$)$_{2,3}$NHCOCH$_2$NHCOCH$_2$—K,

—CONH(CH$_2$)$_{2,3}$NHCOCH$_2$—K,

—CONH(CH$_2$)$_{2,3}$NHCOCH(CH$_3$)—K,

—CON(CH$_2$CH$_2$OH(CH$_2$)$_2$NHCOCH$_2$—K.

Radicals $A^2$ that are mentioned by way of example are:

—NHCOCH(CH$_3$)—K,

—NHCOCH$_2$—K,

—N(CH$_3$)COCH$_2$—K,

—N(CH$_3$)COCH(CH)$_3$—K,

—N(CH$_2$CH$_2$OH)COCH$_2$—K,

—N(CH$_2$CH$_2$OH)COCH(CH$_3$)—K.

The compounds of general formula I according to the invention can be produced according to the process that is known according to one skilled in the art by a triiodo- or tribromoaromatic compound of general formula II

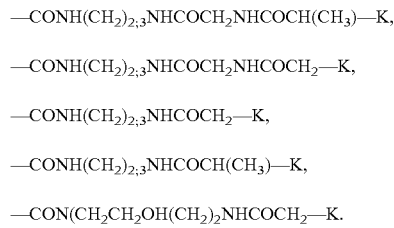
(II)

being reacted in a way that is known in the art with a macrocyclic compound of general formula III

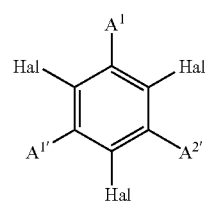
(III)

in which
W stands for a protective group or a —CH$_2$COOX' group with X' in the meaning of X or a protective group, and $A^{1'}$ in the meaning of —CO—NR$^1$—(CH$_2$)$_n$—NR$^2$—(CO—CHZ$^1$—NH)$_m$—CO—CHZ$^2$—Hal' and A$^{2'}$ stands for —NR$^1$—CO—CHZ$^2$—Hal' with Hal' in the meaning of chlorine or bromine, and then optionally protective group W being removed and the radical CH$_2$COOX being introduced in a way that is known in the art or the protective group that optionally stands for X' being removed and then reacted in a way that is known in the art with a metal oxide or metal salt of an element of atomic numbers 20-29, 39, 42, 44 or 57-83.

As amino protective groups W, the benzyloxycarbonyl, tert-butoxycarbonyl, trifluoroacetyl, fluorenylmethoxycarbonyl, benzyl, formyl, 4-methoxybenzyl, 2,2,2-trichloroethoxycarbonyl, phthaloyl, 1,2-oxazoline, tosyl, dithiasuccinoyl, allyloxycarbonyl, sulfate, pent-4-enecarbonyl, 2-chloroacetoxymethyl (or ethyl) benzoyl, tetrachlorophthaloyl, and alkyloxycarbonyl groups that are familiar to one skilled in the art can be mentioned [Th. W. Greene, P. G. M. Wuts, Protective Groups in Organic Syntheses, 2nd Ed., John Wiley and Sons (1991), pp. 309-385; E. Meinjohanns et al, J. Chem. Soc. Pekin Trans 1, 1995, 405; U. Ellensik et al, Carbohydrate Research 280, 1996, 251; R. Madsen et al, J. Org. Chem. 60, 1995, 7920; R. R. Schmidt, Tetrahedron Letters 1995, 5343].

The cleavage of the protective groups is carried out according to the process that is known to one skilled in the art (see, e.g., E. Wünsch, Methoden der Org. Chemie [Methods of Organic Chemistry], Houben-Weyl, Vol. XV/1, 4$^{th}$ Edition 1974, p. 315), for example by hydrolysis, hydrogenolysis, alkaline saponification of esters with alkali in aqueous-alcoholic solution at temperatures from 0° C. to 50° C., acidic saponification with mineral acids, or in the case of Boc groups with the aid of trifluoroacetic acid.

If X' stands for an acid protective group, lower alkyl, aryl and aralkyl groups, for example the methyl, ethyl, propyl, butyl, phenyl, benzyl, diphenylmethyl, triphenylmethyl, bis-(p-nitrophenyl)-methyl group, as well as trialkylsilyl groups, are suitable.

The t-butyl group and the benzyl group are preferred.

The cleavage of the protective groups is carried out according to the processes known to one skilled in the art (see, e.g., E. Wünsch, Methoden der Org. Chemie, Houben-Weyl, Volume XV/1, 4th Edition 1974, p. 315), for example by hydrolysis, hydrogenolysis, alkaline saponification of esters in aqueous-alcoholic solution at temperatures of 0° C. to 50° C., acid saponification with mineral acids or in the case of tert-butyl-esters with the aid of trifluoroacetic acid (Protective Groups in Organic Synthesis, 2$^{nd}$ Edition, T. W. Greene und P. G. M. Wuts, John Wiley and Sons, Inc., New York, 1991).

The introduction of the desired metal ions can be carried out as has been disclosed in Patents EP 71564, EP 130934 and DE-OS 34 01 052. To this end, the metal oxide or a metal salt (for example, a chloride, nitrate, acetate, carbonate or sulfate) of the desired element is dissolved or suspended in water and/or a lower alcohol (such as methanol, ethanol or isopropanol) and reacted with the solution or suspension of the equivalent amount of the complexing agent.

The neutralization of optionally still present free carboxy groups is carried out with the aid of inorganic bases (e.g., hydroxides, carbonates or bicarbonates) of, e.g., sodium, potassium, lithium, magnesium or calcium and/or organic bases, such as, i.a., primary, secondary and tertiary amines, such as, e.g., ethanolamine, morpholine, glucamine, N-methyl- and N,N-dimethylglucamine, as well as basic amino acids, such as, e.g., lysine, arginine, and ornithine or amides of original neutral or acidic amino acids.

For the production of neutral complex compounds, for example in acidic complex salts in aqueous solution or suspension, enough of the desired base can be added to reach the neutral point. The solution that is obtained can then be evaporated to the dry state in a vacuum. It is frequently advantageous to precipitate the neutral salts that are formed by adding water-miscible solvents, such as, e.g., lower alcohols (methanol, ethanol, isopropanol, etc.), lower ketones (acetone, etc.), or polar ethers (tetrahydrofuran, dioxane, 1,2-dimethoxyethane, etc.), and thus to obtain easily isolated and readily purified crystallizates. It has proven especially advantageous to add the desired base as early as during the complexing of the reaction mixture and thus to save a process step.

The purification of the thus obtained complexes is carried out, optionally after the pH is set to 6 to 8, preferably about 7, by adding an acid or base, preferably by ultrafiltration with membranes of a suitable pore size (e.g., Amicon®YM1, Amicon®YM3), gel filtration on, e.g., suitable Sephadex® gels or by HPLC on silica gel or reverse-phase material.

Purification can also be carried out by crystallization from solvents such as methanol, ethanol, i-propanol, acetone or their mixtures with water.

In the case of neutral complex compounds, it is frequently advantageous to add the oligomer complexes via an anion exchanger, for example IRA 67 (OH$^-$ form), and optionally in addition via a cation exchanger, for example IRC 50 (H$^+$ form), to separate ionic components.

The production of the compounds of general formula I according to the invention can be carried out as indicated above:

The reaction of triiodo- or tribromoaromatic compounds of general formula II with compounds of general formula III is carried out according to the process of alkylation of N-containing macrocylic compounds known to one skilled in the art.

In this connection, compounds of general formula II, whereby A$^{1'}$ stands for —CO—NR$^1$—(CH$_2$)$_n$—NR$^2$—(CO—CHZ$^1$—NH)$_m$—CO—CHZ$^2$Hal' and A$^{2'}$ stands for —NR$^1$—CO—CHZ$^2$Hal', with Hal' in the meaning of chlorine or bromine, are alkylated with the free amine of III by being reacted in aprotic solvents such as acetonitrile, methylene chloride, chloroform, DMF, DMA, THF, dioxane or toluene at temperatures of 0°-80° C., optionally with the addition of an organic or inorganic base, such as NEt$_3$, pyridine, DMAP, Hünig base, Na$_2$CO$_3$, or CaCO$_3$.

The production of the compounds of general formula II, whereby A$^{1'}$ stands for —CO—NR$^1$—(CH$_2$)$_n$—NR$^2$—(CO—CHZ$^1$—NH)$_m$—CO—CHZ$^2$Hal' and A$^{2'}$ stands for —NR$^1$—CO—CHZ$^2$Hal', with Hal' in the meaning of chlorine or bromine, is carried out according to the process of acylation of amines of general formula II known to one skilled in the art, whereby A$^{1'}$ stands for —CO—NR$^1$—(CH$_2$)$_n$—NR$^2$—(CO—CHZ$^1$—NH)$_m$H and A$^{2'}$ stands for —NR$^1$H, with chloroacetyl chloride, chloroacetyl bromide, bromoacetyl bromide, 2-bromopropionylbromide, 2-bromopropionyl chloride or 2-chloropropionyl chloride in aprotic solvents such as acetonitrile, methylene chloride, chloroform, DMF, DMA, THF, dioxane or toluene at temperatures of 0°-40° C., optionally with the addition of an organic or inorganic base, such as NEt$_3$, pyridine, DMAP, Hünig base, Na$_2$CO$_3$, or CaCO$_3$.

The production of amines of general formula II, whereby A$^{1'}$ stands for —CO—NR$^1$—(CH$_2$)$_n$—NR$^2$—CO—CHZ$^1$—NH)$_m$—H and A$^{2'}$ stands for —NR$^1$H, is carried out by reactions of compounds of general formula IV

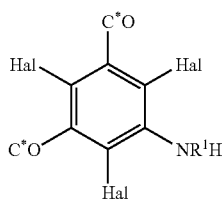

(IV)

with diamines of general formula A

HNR$^1$—(CH$_2$)$_n$—NR$^2$H  (A), in which C*O stands for a —COOH group or activated carboxyl group, and Hal, R$^1$, R$^2$, and n are in the above-indicated meaning, according to the methods for amide formation known to one skilled in the art (see above), in an aprotic solvent such as DMF, DMA, THF, dioxane, 1,2-dichloroethane, chloroform, dichloromethane or toluene optionally with the addition of an organic or inorganic base, such as NEt$_3$, pyridine, DMAP, Hünig base, Na$_2$CO$_3$, K$_2$CO$_3$, or CaCO$_3$ at temperatures of 0° C.-100° C.

In many cases, it has proven advantageous to use the diamine itself as a solvent. At times, it may be advantageous to use one of the two terminal amino groups in protected form (e.g., Mono-Boc, Mono-Z) and to cleave this protective group according to the methods known to one skilled in the art after the coupling is completed (T. W. Greene, see above).

The diamines or mono-protected diamines are known in the literature and can be purchased (e.g., Aldrich, Fluka). The acid chlorides of the compounds of general formula IV are preferably used.

The production of the compound

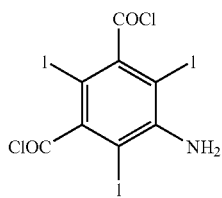

is described in DE 2943777.

The production of the compound

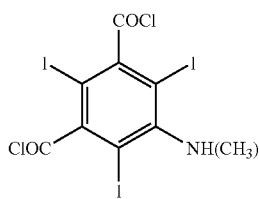

is described in EP 0033426.

The production of the corresponding tri-bromine compounds is carried out analogously to what is described in EP 0073715.

Compounds of general formula III, such as, e.g., Tri-Boc cyclene, Tri-Z-cyclene, Tri-TFA-cyclene or tris-tert-butyl-DO3A are known in the literature.

The compounds according to the invention can be used both in x-ray diagnosis and in MR diagnosis.

The high x-ray opacity paired with the good water-solubility thereof of the halogenated x-ray contrast media is combined with the intense hydrophilia of metal chelates and good compatibility in a molecule that is inherent in them. The very high hydrophilia of the new compounds results in that the side-effect profile corresponds to that of the very well-tolerated Gd compounds, as they are used in MR imaging. This property therefore makes it especially suitable for use in patients with a proven allergy to iodized compounds or in the case of existing atopy. In particular, the incidence of severe side effects such as bronchial spasms and shock or even death is reduced to the low level of the MR contrast medium.

The low osmolality of the formulations is an indication of a generally very good compatibility of the new compounds. They are therefore especially suitable for intravascular (parenteral) uses.

Depending on the pharmaceutical formulation, the contrast media can be used exclusively for x-ray diagnosis (trihalogen complexes with diamagnetic metals), but also simultaneously for x-ray diagnosis and MRT diagnosis (trihalogen complexes with paramagnetic atoms, preferably Gd). The compounds can very advantageously be used in, e.g., urography, computer tomography, angiography, gastrography, mammography, cardiology and neuroradiology. Even in the case of radiation therapy, the complexes that are used are advantageous. The compounds are suitable for all perfusion measurements. A differentiation of areas that are well supplied with blood and ischemic areas is possible after intravascular injection. Quite generally, these compounds can be used in all indications where conventional contrast media are used in x-ray diagnosis or MR diagnosis.

The new contrast media can also be used for the magnetization-transfer technique (see, e.g., Journ. Chem. Phys. 39(11), 2892 (1963), as well as WO 03/013616), if they contain mobile protons in their chemical structure.

The contrasting of cerebral infarctions and tumors of the liver or space-occupying processes in the liver as well as of tumors of the abdomen (including the kidneys) and the muscle-skeleton system is especially valuable diagnostically. Based on the low osmotic pressure, the blood vessels can be visualized especially advantageously after intraarterial injection or else intravenous injection.

If the compound according to the invention is intended for use in MR diagnosis, the metal ion of the signaling group must be paramagnetic. These are in particular the divalent and trivalent ions of the elements of atomic numbers 21-29, 42, 44 and 58-70. Suitable ions are, for example, the chromium(III), iron(II), cobalt(II), nickel(II), copper(II), praseodymium(III), neodymium(III), samarium(III) and ytterbium(III) ion. Because of their strong magnetic moment, gadolinium(III), terbium(III), dysprosium(III), holmium(III), erbium(III), iron(III) and manganese(II) ions are preferred; gadolinium(III) and manganese(II) ions are especially preferred.

If the compound according to the invention is intended for use in x-ray diagnosis, the metal ion is preferably derived from an element of a higher atomic number to achieve an adequate absorption of the x-rays. It was found that for this purpose, diagnostic agents that contain a physiologically compatible complex salt with metal ions of elements of atomic numbers 25, 26 and 39 as well as 57-83 are suitable.

Manganese(II), iron(II), iron(III), praseodymium(III), neodymium(III), samarium(III), gadolinium(III), ytterbium(III) or bismuth(III) ions, especially dysprosium(III) ions and yttrium(III) ions, are preferred.

The production of the pharmaceutical agents according to the invention is carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepenta-acetic acid or the Ca complexes that correspond to the metal complexes according to the invention) or—if necessary—electrolytes such as, for example, sodium chloride, or—if necessary—antioxidants, such as, for example, ascorbic acid.

If suspensions or solutions of the agents according to the invention in water or physiological salt solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention without isolating the complexes. In any case, special care must be taken to perform the chelation so that the complexes according to the invention are virtually free of noncomplexed metal ions that have a toxic effect.

This can be ensured, for example, with the aid of color indicators such as xylenol orange by control titrations during the production process. The invention therefore also relates to the process for the production of complex compounds and their salts. As a final precaution, there remains purification of the isolated complex.

In the in-vivo administration of the agents according to the invention, the latter can be administered together with a suitable vehicle, such as, for example, serum or physiological common salt solution, and together with another protein such as, for example, human serum albumin (HSA).

The agents according to the invention are usually administered parenterally, preferably i.v. They can also be administered intraarterially or interstitially/intracutaneously, depending on whether a vessel/organ is to be visualized selectively contrasted (e.g., visualization of the coronary arteries after intraarterial injection) or tissue or pathologies (e.g., diagnosis of cerebral tumors after intravenous injection).

The pharmaceutical agents according to the invention contain preferably 0.001-1 mol/l of the above-mentioned compound and are generally dosed in amounts of 0.001-5 mmol/kg.

The agents according to the invention meet the many requirements for suitability as contrast media for magnetic resonance tomography. After oral or parenteral administration by increasing the signal intensity, they are extremely well suited for enhancing the informational value of the image that is obtained with the aid of an MR tomograph. They also show the high effectiveness that is necessary to load the body with the minimum possible amounts of foreign substances and the good compatibility that is necessary to maintain the non-invasive nature of the studies. The high effectiveness (relaxivity) of the paramagnetic compounds according to the invention is of great advantage for use in magnetic resonance tomography. Thus, the relaxivity (L/mmol$^{-1}$*sec$^{-1}$ of gadolinium-containing compounds) is generally 2 to 4× greater than in conventional Gd complexes (e.g., gadobutrol).

The good water solubility and low osmolality of the agents according to the invention makes it possible to produce highly concentrated solutions, so as to keep the volume burden of the circulatory system within reasonable limits and to offset the dilution by bodily fluids. In addition, the agents according to the invention exhibit not only high stability in-vitro, but also surprisingly high stability in-vivo, so that a release or an exchange of the ions, which are inherently toxic and are bonded in the complexes, is carried out only extremely slowly within the time that it takes for the new contrast media to be completely excreted again.

In general, the agents according to the invention are dosed for use as MRT diagnostic agents in amounts of 0.001-5 mmol of Gd/kg, preferably 0.005-0.5 mmol of Gd/kg.

The agents according to the invention are extremely well suited as x-ray contrast media, whereby it is especially to be emphasized that with them, no signs of the anaphylaxis-like reactions that are known from the iodine-containing contrast media can be detected in biochemical-pharmacological studies. In the case of strong x-ray absorption, they are especially effective in areas of higher tube voltages (e.g., CT and DSA).

In general, the agents according to the invention are dosed for administration as x-ray contrast media analogously to, for example, meglumine-diatrizoate, in amounts of 0.01-5 mmol/kg, preferably 0.02-1 mmol of substance/kg, which corresponds to 0.06-6 mmol (I+Dy)/kg in the case of, e.g., iodine-Dy compounds. Depending on the diagnostic requirement, formulations can be selected that can be used both in x-ray diagnosis and in MR diagnosis. To achieve optimal results for both imaging modalities, it may be advantageous to select formulations in which the proportion of paramagnetic ions is reduced, since for many MR diagnostic applications, a point of diminishing returns is reached with too high a proportion of paramagnetic ions.

For dual uses, formulations can be used in which the proportion, in percent, of paramagnetic substances (e.g., Gd) is reduced to 0.05 to 50, preferably to 2-20%. As an example, a cardiac diagnostic application can be mentioned. For the examination, a formulation that consists of the substances according to the invention in a total concentration of, e.g., 0.25 mol/l is used. The proportion of Gd-containing complexes is 20%; the remaining 80% of the metals are, e.g., Dy atoms. In an x-ray coronary angiography after intraarterial or intravenous administration, e.g., 50 ml is used, i.e., 0.18 mmol of substance per kg of body weight in a patient who weighs 70 kg. Shortly after x-ray visualization of the coronary vessels has taken place, an MR diagnosis of the heart is followed to be able to differentiate vital myocardial areas from necrotic myocardial areas. The amount of about 110 µmol of Gd/kg previously administered for the test is optimal for this purpose.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

PATENT EXAMPLES

Example 1 a) N,N-Bis-(2-aminoethyl)-5-(methylamino)-2,4,6-triiodo-isophthalic acid amide

A solution of 10 g (16.4 mmol) of 2,4,6-triiodo-5-(methylamino)-isophthalic acid dichloride (EP 0033426, Sovak, 1/80 US) in 100 ml of tetrahydrofuran is added in drops to 26.7 ml (399 mmol) of ethylenediamine over 1 hour at room temperature and stirred for 14 more hours. The precipitated solid is filtered off, rewashed with ethanol, taken up in 100 ml of water, and set at a pH of 8.0 with 1 M lithium hydroxide solution. After concentration by evaporation in a vacuum, it is recrystallized from ethanol.

Yield: 8.7 g (81% of theory) of a colorless solid
Elementary analysis:
Cld.: C 23.77 H 2.76 N 10.66 I 57.94
Fnd.: C 23.98 H 2.71 N 10.62 I 57.68 b) N,N-Bis-[2-(2-bromopropionylamino)ethyl)-5-[(2-bromopropionyl)methylamino]-2,4,6-triiodoisophthalic acid amide 50 g (76.1 mmol) of N,N-bis-(2-aminoethyl)-5-(methylamino)-2,4,6-triiodoisophthalic acid amide is dissolved in 500 ml of dimethylacetamide, and 75.5 g (350 mmol) of 2-bromopropionic acid bromide (Aldrich) is added in drops over 15 minutes at 0° C. Then, it is stirred for 20 hours at 40° C. The reaction mixture is poured into 4000 ml of ice water, the accumulating solid is filtered off, dissolved in 800 ml of ethyl acetate and extracted three times with 250 ml each of water. The organic phase is dried on sodium sulfate, and the solvent is evaporated to the dry state. The crude product is recrystallized from methyl-tert-butyl ether.

Yield: 57 g (71% of theory) of a colorless solid
Elementary analysis:
Cld.: C 24.88 H 2.56 N 6.60
Fnd.: C 25.21 H 2.63 N 6.71 c) 2,4,6-Triiodo-5-(2-{10-[1,4,7-tris-(benzyloxycarbonyl)-1,4,7,10-tetraazacyclododecanyl]}-propionyl)methylaminoisophthalic acid-N,N-bis-(3-aza-5-methyl-4-oxopentane-1,5-diyl-{10-[1,4,7-tris-(benzyloxycarbonyl)-1,4,7,10-tetraazacyclododecanyl]})amide 111.6 g (194.2 mmol) of 1,4,7-tris-(benzyloxycarbonyl)-1,4,7,10-tetrazcyclododecane (Delaney et al., *J. Chem. Soc. Perkin Trans.* 1991, 3329) is dissolved in 800 ml of acetonitrile and mixed with 53.7 g (388.4 mmol) of sodium carbonate. Then, while being stirred vigorously, 55 g (51.8 mmol) of N,N-bis-[2-(2-bromopropionylamino)ethyl)-5-[(2-bromopropionyl)methylamino]-2,4,6-triiodoisophthalic acid amide is added, and it is refluxed for 20 hours. Insoluble components are filtered out, it is evaporated to the dry state, and the residue is chromatographed on silica gel (mobile solvent: dichloromethane/methanol 20:1). The fractions that contain the product are combined and concentrated by evaporation.

Yield: 51.1 g (39% of theory) of a colorless solid
Elementary analysis:
Cld.: C 55.73 H 5.47 N 9.36 I 14.97
Fnd.: C 55.91 H 5.44 N 9.38 I 14.89 d) 2,4,6-Triiodo-5-[2-(1,4,7,10-tetraazacyclododecanyl)propionyl]methylaminoisophthalic acid-N,N-bis-[3-aza-5-methyl-4-oxopentane-1,5-diyl-(1,4,7,10-tetraazacyclododecan-yl)]amide 50 g (19.7 mmol) of 2,4,6-triiodo-5-(2-{10-[1,4,7-tris-(benzyloxycarbonyl)-1,4,7,10-tetraazacyclododecanyl]}propionyl)methylaminoisophthalic acid-N,N-bis-(3-aza-5-methyl-4-oxopentane-1,5-diyl-{10-[1,4,7-tris-(benzyloxycarbonyl)-1,4,7,10-tetraazacyclodo-decanyl]}) amide is carefully mixed at 0-5° C. with 500 ml of HBr/AcOH (33%), and it is stirred for 3 hours at room temperature. Then, the reaction mixture is poured into 2500 ml of diethyl ether, the solid that accumulates in this case is suctioned off and rewashed several times with diethyl ether. The residue is dissolved in 300 ml of water and 300 ml of dichloromethane while being stirred vigorously, and 32% NaOH solution is added until a pH of 10 is reached. The organic phase is separated, the aqueous phase is extracted three times with 150 ml each of dichloromethane, and the combined organic phases are dried on magnesium sulfate and evaporated to the dry state.

Yield: 24.4 g (93% of theory) of a colorless solid
Elementary analysis:
Cld.: C 41.36 H 6.34 N 17.82 I 28.50
Fnd.: C 41.49 H 6.37 N 17.76 I 28.39 e) 2,4,6-Triiodo-5-(2-{10-[1,4,7-tris-(carboxymethyl)-1,4,7,10-tetraazacyclododecanyl]}propionyl)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl]})amide 23.8 g (17.8 mmol) of 2,4,6-triiodo-5-[2-(1,4,7,10-tetraazacyclododecanyl)propionyl]-methylaminoisophthalic acid-N,N-bis-[3-aza-5-methyl-4-oxopentane-1,5-diyl-(1,4,7,10-tetraazacyclododecan-yl)]amide is dissolved in 200 ml of water, 25.7 g (272.7 mmol) of chloroacetic acid is added, and a pH of 9.5 is set at 60° C. with 32% NaOH. It is heated for 10 hours to 70° C., whereby the pH of the reaction mixture is continuously reset to 9.5. After cooling to room temperature, a pH of 1 is set with concentrated HCl, and the solution is concentrated by evaporation in a vacuum. The residue is absorptively precipitated with 300 ml of methanol, insoluble components are filtered out, and the filtrate is concentrated by evaporation. The residue is dissolved in 200 ml of water and added to an ion-exchange column (1200 ml, IR 120, $H^+$-form). Then, it is washed with 5 l of water, and the acid eluate is concentrated by evaporation. The residue is dissolved in 150 ml of methanol and added in drops in 2500 ml of diethyl ether, the solid that accumulates in this case is suctioned off, rewashed several times with diethyl ether and dried in a vacuum.

Yield: 24.1 g (73% of theory) of a colorless solid
Elementary analysis:
Cld.: C 41.37 H 5.53 N 12.81 I 20.49
Fnd.: C 41.54 H 5.57 N 12.77 I 20.31 f) 2,4,6-Triiodo-5-(2-{10-[1,4,7-tris-(carboxymethyl)-1,4,7,10-tetraazacyclododecanyl]}propionyl, Gd-complex)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl,Gd-complex]})amide 12.8 g (6.9 mmol) of 2,4,6-triiodo-5-(2-{10-[1,4,7-tris-(carboxymethyl)-1,4,7,10-tetraazacyclododecanyl]}propionyl)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl]})amide is dissolved in 100 ml of water and acidified by adding 3 ml of acetic acid. 3.7 g (10.4 mmol) of gadolinium oxide is added, and it is refluxed for 6 hours. After the complexing is completed, it is set at pH 7.4 with ammonia and chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 9.9 g (58% of theory) of a colorless solid
Water content (Karl-Fischer): 6.4%
Elementary analysis (relative to the anhydrous substance):
Cld.: C 33.12 H 4.04 N 10.26 I 16.40 Gd 20.33
Fnd.: C 33.31 H 4.08 N 10.23 I 16.31 Gd 20.27

Example 2

2,4,6-Triiodo-5-(2-{10-[1,4,7-tris-(carboxymethyl)-1,4,7, 10-tetraazacyclododecanyl]}propionyl, Dy-complex)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl, Dy-complex]})amide 12.8 g (6.9 mmol) of 2,4,6-triiodo-5-(2-{10-[1,4,7-tris-(carboxymethyl)-1,4,7,10-tetraazacyclododecanyl]}propionyl)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl]})amide (title compound 1e) is dissolved in 100 ml of water and acidified by adding 3 ml of acetic acid. 3.9 g (10.4 mmol) of dysprosium oxide is added and refluxed for 6 hours. After complexing is completed, it is set at a pH of 7.4 with ammonia and chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then it is absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 11.2 g (64% of theory) of a colorless solid
Water content (Karl-Fischer): 7.5%
Elementary analysis (relative to the anhydrous substance):
Cld.: C 32.90 H 4.01 N 10.19 I 16.29 Dy 20.86
Fnd.: C 33.03 H 4.05 N 10.17 I 16.22 Dy 20.65

Example 3

2,4,6-Triiodo-5-(2-{10-[1,4,7-tris-(carboxymethyl)-1,4,7, 10-tetraazacyclododecanyl]}propionyl, Yb-complex)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl, Yb-complex]})amide 12.8 g (6.9 mmol) of 2,4,6-triiodo-5-(2-{10-[1,4,7-tris-(carboxymethyl)-1,4,7,10-tetraazacyclododecanyl]}propionyl)methylaminoisophthalic acid-N,N-bis-(3-aza-5-methyl-4-oxopentane-1,5-diyl-{10-[1,4,7-tris-(carboxymethyl)-1,4, 7,10-tetraazacyclododecanyl]})amide (title compound 1e) is dissolved in 100 ml of water and acidified by adding 3 ml of acetic acid. 4.1 g (10.4 mmol) of ytterbium oxide is added, and it is refluxed for 6 hours. After complexing is completed, a pH of 7.4 is set with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 9.5 g (54% of theory) of a colorless solid
Water content (Karl-Fischer): 6.7%
Elementary analysis (relative to the anhydrous substance):
Cld.: C 32.46 H 3.96 N 10.05 I 16.07 Yb 21.92
Fnd.: C 32.61 H 4.00 N 9.97 I 15.98 Yb 21.79

Example 4

2,4,6-Triiodo-5-(2-{10-[1,4,7-tris-(carboxymethyl)-1,4,7, 10-tetraazacyclododecanyl]}propionyl, Y-complex)methylaminoisophthalic acid-N,N-bis-(3-aza-5-methyl-4-oxopentane-1,5-diyl-{10-[1,4,7-tris-(carboxymethyl)-1,4,7,10-tetraazacyclododecanyl, Y-complex]})amide 12.8 g (6.9 mmol) of 2,4,6-triiodo-5-(2-{10-[1,4,7-tris-(carboxymethyl)-1,4,7,10-tetraazacyclododecanyl]}propionyl)methylaminoisophthalic acid-N,N-bis-(3-aza-5-methyl-4-oxopentane-1,5-diyl-{10-[1,4,7-tris-(carboxymethyl)-1,4, 7,10-tetraazacyclododecanyl]})amide (title compound 1e) is dissolved in 100 ml of water and acidified by adding 3 ml of acetic acid. 2.35 g (10.4 mmol) of yttrium oxide is added, and it is refluxed for 6 hours. After complexing is completed, a pH of 7.4 is set with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.8 g (50% of theory) of a colorless solid
Water content (Karl-Fischer): 5.9%
Elementary analysis (relative to the anhydrous substance):
Cld.: C 36.33 H 4.43 N 11.25 I 17.99 Y 12.60
Fnd.: C 36.52 H 4.49 N 11.28 I 17.81 Y 12.40

Example 5 a) N,N-Bis-[2-(bromoacetylamino)ethyl]-5-[(bromoacetyl)methylamino]-2,4,6-triiodoisophthalic acid amide 50 g (76.1 mmol) of N,N-bis-(2-aminoethyl)-5-(methylamino)-2,4,6-triiodoisophthalic acid amide (title compound 1a) is dissolved in 500 ml of dimethylacetamide, and at 0° C., 70.6 g (350 mmol) of bromoacetyl bromide (Aldrich) is added in drops over 15 minutes. Then, it is stirred for 20 hours at 40° C. The reaction mixture is poured into 4000 ml of ice water, the accumulating solid is filtered off, dissolved in 800 ml of ethyl acetate and extracted three times with 250 ml each of water. The organic phase is dried on sodium sulfate, and the solvent is evaporated to the dry state. The crude product is recrystallized from methyl-tert-butyl ether.

Yield: 60 g (77% of theory) of a colorless solid
Elementary analysis:
Cld.: C 22.38 H 2.08 N 6.87
Fnd.: C 22.63 H 2.21 N 6.75 b) 2,4,6-Triiodo-5-({10-[1,4,7-tris-(benzyloxycarbonyl)-1, 4,7,10-tetraazacyclododecanyl]}-acetyl)methylaminoisophthalic acid-N,N-bis-(3-aza-4-oxopentane-1,5-diyl-{10-[1,4, 7-tris-(benzyloxycarbonyl)-1,4,7,10-tetraazacyclododecanyl]})amide 122.5 g (213.2 mmol) of 1,4,7-tris-(benzyloxycarbonyl)-1,4,7,10-tetrazacyclododecane (Delaney et al., *J. Chem. Soc. Perkin Trans.* 1991, 3329) is dissolved in 800 ml of acetonitrile and mixed with 60 g (426.4 mmol) of sodium carbonate. Then, while being stirred vigorously, 58 g (56.9 mmol) of N,N-bis-[2-(bromoacetylamino)ethyl]-5-[(bromoacetyl)methylamino]-2,4,6-triiodoisophthalic acid amide is added and refluxed for 20 hours. Insoluble components are filtered out, evaporated to the dry state, and the residue is chromatographed on silica gel (mobile solvent: dichloromethane/methanol 20:1). The fractions that contain the product are combined and concentrated by evaporation.

Yield: 142 g (54% of theory) of a colorless solid
Elementary analysis:
Cld.: C 55.23 H 5.32 N 9.52 I 15.22
Fnd.: C 55.41 H 5.35 N 9.48 I 15.13 c) 2,4,6-Triiodo-5-[(1,4,7,10-tetraazacyclododecanyl) acetyl]methylaminoisophthalic acid-N,N-bis-[3-aza-4-oxo-pentane-1,5-diyl-(1,4,7,10-tetraazacyclododecanyl)]amide 100 g (40 mmol) of 2,4,6-triiodo-5-({10-[1,4,7-tris-(benzyloxycarbonyl)-1,4,7,10-tetraazacyclododecanyl]}acetyl) methylaminoisophthalic acid-N,N-bis-(3-aza-4-oxopentane-1,5-diyl-{10-[1,4,7-tris-(benzyloxycarbonyl)-1,4,7,10-tetraazacyclododecanyl]})amide is carefully mixed at 0-5° C. with 800 ml of HBr/AcOH (33%), and it is stirred for 3 hours at room temperature. Then, the reaction mixture is poured into 4000 ml of diethyl ether, the solid that accumulates in this case is suctioned off, and it is rewashed several times with diethyl ether. The residue is dissolved in 500 ml of water and 500 ml of dichloromethane while being stirred vigorously, and 32% NaOH solution is added until a pH of 10 is reached. The organic phase is separated, the aqueous phase is extracted three times with 250 ml each of dichloromethane, and the combined organic phases are dried on magnesium sulfate and evaporated to the dry state.

Yield: 48.7 g (94% of theory) of a colorless solid
Elementary analysis:
Cld.: C 39.92 H 6.08 N 18.40 I 29.42
Fnd.: C 40.19 H 6.13 N 18.36 I 29.27 d) 2,4,6-Triiodo-5-({10-[1,4,7-tris-(carboxymethyl)-1,4,7,10-tetraazacyclododecanyl]}acetyl)methylaminoisophthalic acid-N,N-bis-(3-aza-4-oxopentane-1,5-diyl-{10-[1,4,7-tris-(carboxymethyl)-1,4,7,10-tetraazacyclododecanyl]})amide 45 g (34.8 mmol) of 2,4,6-triiodo-5-[(1,4,7,10-tetraazacyclododecanyl)acetyl]methylaminoisophthalic acid-N,N-bis-[3-aza-4-oxopentane-1,5-diyl-(1,4,7,10-tetraazacyclododecanyl)]amide is dissolved in 400 ml of water, 50.2 g (532.8 mmol) of chloroacetic acid is added, and a pH of 9.5 is set at 60° C. with 32% NaOH. It is heated for 10 hours to 70° C., whereby the pH of the reaction mixture is reset continuously to 9.5. After cooling to room temperature, a pH of 1 is set with concentrated HCl, and the solution is concentrated by evaporation in a vacuum. The residue is absorptively precipitated with 300 ml of methanol, insoluble components are filtered out, and the filtrate is concentrated by evaporation. The residue is dissolved in 300 ml of water and added to an ion-exchange column (1200 ml, IR 120, H$^+$-form). Then, it is washed with 5 l of water, and the acid eluate is concentrated by evaporation. The residue is dissolved in 250 ml of methanol and added in drops in 4500 ml of diethyl ether, the solid that accumulates in this case is suctioned off, rewashed several times with diethyl ether and dried in a vacuum.

Yield: 49.9 g (79% of theory) of a colorless solid
Elementary analysis:
Cld.: C 40.34 H 5.33 N 13.11 I 20.96
Fnd.: C 40.57 H 5.34 N 13.07 I 20.77 e) 2,4,6-Triiodo-5-({10-[1,4,7-tris-(carboxymethyl)-1,4,7,10-tetraazacyclododecanyl]}acetyl, Gd-complex)methylaminoisophthalic acid-N,N-bis-(3-aza-4-oxopentane-1,5-diyl-{10-[1,4,7-tris-(carboxymethyl)-1,4,7,10-tetraazacyclododecanyl, Gd-complex]})amide 12.5 g (6.9 mmol) of 2,4,6-triiodo-5-({10-[1,4,7-tris-(carboxymethyl)-1,4,7,10-tetraazacyclododecanyl]}acetyl)methylaminoisophthalic acid-N,N-bis-(3-aza-4-oxopentane-1,5-diyl-{10-[1,4,7-tris-(carboxymethyl)-1,4,7,10-tetraazacyclododecanyl]})amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 8.7 g (52% of theory) of a colorless solid
Water content (Karl-Fischer): 5.8%
Elementary analysis (relative to the anhydrous substance):
Cld.: C 32.15 H 3.85 N 10.45 I 16.71 Gd 20.70
Fnd.: C 32.39 H 3.88 N 10.51 I 16.59 Gd 20.51

Example 6 a) N,N-Bis-(2-aminoethyl)-5-amino-2,4,6-triiodoisophthalic acid amide

A solution of 10 g (16.8 mmol) of 5-amino-2,4,6-triiodo-isophthalic acid—dichloride (DE 2943777, Schering A G, (priority: 10/26/79)) in 100 ml of tetrahydrofuran is added in drops to 26.7 ml (399 mmol) of ethylenediamine over 1 hour at room temperature, and stirring is continued for 14 hours. The precipitated solid is filtered off, rewashed with ethanol, taken up in 100 ml of water and set at a pH of 8.0 with 1 M lithium hydroxide solution. After concentration by evaporation in a vacuum, it is recrystallized from ethanol.

Yield: 8.3 g (77% of theory) of a colorless solid
Elementary analysis:
Cld.: C 22.42 H 2.51 N 10.89 I 59.21
Fnd.: C 22.84 H 2.62 N 10.99 I 58.89 b) N,N-Bis-[2-(2-bromopropionylamino)ethyl]-5-[(2-bromopropionyl)amino]-2,4,6-triiodoisophthalic acid amide 50 g (77.8 mmol) of N,N-bis-(2-aminoethyl)-5-amino-2,4,6-triiodoisophthalic acid amide is dissolved in 500 ml of dimethylacetamide, and 75.5 g (350 mmol) of 2-bromopropionic acid bromide (Aldrich) is added in drops over 15 minutes at 0° C. Then, it is stirred for 20 hours at 40° C. The reaction mixture is poured into 4000 ml of ice water, the accumulating solid is filtered off, dissolved in 800 ml of ethyl acetate, and extracted three times with 250 ml each of water. The organic phase is dried on sodium sulfate, and the solvent is evaporated to the dry state. The crude product is recrystallized from methyl-tert-butyl ether.

Yield: 45 g (55% of theory) of a colorless solid
Elementary analysis:
Cld.: C 24.07 H 2.40 N 6.68
Fnd.: C 24.29 H 2.46 N 6.58 c) 2,4,6-Triiodo-5-(2-{10-[1,4,7-tris-(benzyloxycarbonyl)-1,4,7,10-tetraazacyclododecanyl]}-propionyl)aminoisophthalic acid-N,N-bis-(3-aza-5-methyl-4-oxopentane-1,5-diyl-{10-[1,4,7-tris-(benzyloxycarbonyl)-1,4,7,10-tetraazacyclododecanyl]})amide 90.5 g (157.5 mmol) of 1,4,7-tris-(benzyloxycarbonyl)-1,4,7,10-tetrazacyclododecane (Delaney et al., *J. Chem. Soc. Perkin Trans.* 1991, 3329) is dissolved in 800 ml of acetonitrile and mixed with 43.6 g (315 mmol) of sodium carbonate. Then, 44 g (42 mmol) of N,N-bis-[2-(2-bromopropionylamino)ethyl]-5-[(2-bromopropionyl)amino]-2,4,6-triiodoisophthalic acid amide is added while being stirred vigorously, and it is refluxed for 20 hours. Insoluble components are filtered out, it is evaporated to the dry state, and the residue is chromatographed on silica gel (mobile solvent: dichloromethane/methanol 20:1). The fractions that contain the product are combined and concentrated by evaporation.

Yield: 48.9 g (46% of theory) of a colorless solid
Elementary analysis:
Cld.: C 55.56 H 5.42 N 9.41 I 14.05
Fnd.: C 55.72 H 5.44 N 9.32 I 13.96 d) 2,4,6-Triiodo-5-[2-(1,4,7,10-tetraazacyclododecanyl)propionyl]aminoisophthalic acid-N,N-bis-[3-aza-5-methyl-4-oxopentane-1,5-diyl-(1,4,7,10-tetraazacyclododecanyl)]amide 48 g (19 mmol) of 2,4,6-triiodo-5-(2-{10-[1,4,7-tris-(benzyloxycarbonyl)-1,4,7,10-tetraazacyclododecanyl]}propionyl)aminoisophthalic acid-N,N-bis-(3-aza-5-methyl-4-oxopentane-1,5-diyl-{10-[1,4,7-tris-(benzyloxycarbonyl)-1,4,7,10-tetraazacyclododecanyl]})amide is carefully mixed at 0-5° C. with 500 ml of HBr/AcOH (33%), and it is stirred for 3 hours at room temperature. Then, the reaction mixture is poured into 2500 ml of diethyl ether, the solid that accumulates in this case is suctioned off, and it is rewashed several times with diethyl ether. The residue is dissolved in 300 ml of water and 300 ml of dichloromethane while being stirred vigorously, and 32% NaOH solution is added until a pH of 10 is reached. The organic phase is separated, the aqueous phase is extracted three times with 150 ml each of dichloromethane, and the combined organic phases are dried on magnesium sulfate and evaporated to the dry state.

Yield: 24.3 g (97% of theory) of a colorless solid
Elementary analysis:
Cld.: C 40.89 H 6.25 N 18.01 I 28.80
Fnd.: C 41.04 H 6.27 N 17.96 I 28.63 e) 2,4,6-Triiodo-5-(2-{10-[1,4,7-tris-(carboxymethyl)-1,4,7,10-tetraazacyclododecanyl]}-propionyl)aminoisophthalic acid-N,N-bis-(3-aza-5-methyl-4-oxopentane-1,5-diyl-{10-[1,4,7-tris-(carboxymethyl)-1,4,7,10-tetraazacyclododecanyl]})amide 20 g (15.1 mmol) of 2,4,6-triiodo-5-[2-(1,4,7,10-tetraazacyclododecanyl)propionyl]aminoisophthalic acid-N,N-bis-[3-aza-5-methyl-4-oxopentane-1,5-diyl-(1,4,7,10-tetraazacyclododecanyl)]amide is dissolved in 200 ml of water, 21.8 g (231.8 mmol) of chloroacetic acid is added, and a pH of 9.5 is set at 60° C. with 32% NaOH. It is heated for 10 hours to 70° C., whereby the pH of the reaction mixture is continuously reset to 9.5. After cooling to room temperature, a pH of 1 is set with concentrated HCl, and the solution is concentrated by evaporation in a vacuum. The residue is absorptively precipitated with 300 ml of methanol, insoluble components are filtered out, and the filtrate is concentrated by evaporation. The residue is dissolved in 200 ml of water and added to an ion-exchange column (1200 ml, IR 120, H+-form). Then, it is washed with 5 l of water, and the acid eluate is concentrated by evaporation. The residue is dissolved in 150 ml of methanol and added in drops in 2500 ml of diethyl ether, the solid that accumulates in this case is suctioned off, rewashed several times with diethyl ether and dried in a vacuum.

Yield: 18.7 g (67% of theory) of a colorless solid
Elementary analysis:
Cld.: C 41.03 H 5.47 N 12.91 I 20.64
Fnd.: C 41.27 H 5.52 N 12.88 I 20.55 f) 2,4,6-Triiodo-5-(2-{10-[1,4,7-tris-(carboxymethyl)-1,4,7,10-tetraazacyclododecanyl]}propionyl, Gd-complex)aminoisophthalic acid-N,N-bis-(3-aza-5-methyl-4-oxopentane-1,5-diyl-{10-[1,4,7-tris-(carboxymethyl)-1,4,7,10-tetraazacyclododecanyl, Gd-complex]})amide 12.7 g (6.9 mmol) of 2,4,6-triiodo-5-(2-{10-[1,4,7-tris-(carboxymethyl)-1,4,7,10-tetraazacyclododecanyl]}propionyl)aminoisophthalic acid-N,N-bis-(3-aza-5-methyl-4-oxopentane-1,5-diyl-{10-[1,4,7-tris-(carboxymethyl)-1,4,7,10-tetraazacyclododecanyl]})amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 11 g (64% of theory) of a colorless solid
Water content (Karl-Fischer): 7.3%
Elementary analysis (relative to the anhydrous substance):
Cld.: C 32.80 H 3.98 N 10.32 I 16.50 Gd 20.45
Fnd.: C 33.02 H 4.00 N 10.28 I 16.43 Gd 20.31

Example 7 a) N,N-Bis-[2-(bromoacetylamino)ethyl]-5-[(bromoacetyl)amino]-2,4,6-triiodoisophthalic acid amide 50 g (77.8 mmol) of N,N-bis-(2-aminoethyl)-5-amino-2,4,6-triiodoisophthalic acid amide (title compound 6a) is dissolved in 500 ml of dimethylacetamide, and 70.6 g (350 mmol) of bromoacetyl bromide (Aldrich) is added in drops over 15 minutes at 0° C. Then, it is stirred for 20 hours at 40° C. The reaction mixture is poured into 4000 ml of ice water, the accumulating solid is filtered off, dissolved in 800 ml of ethyl acetate and extracted three times with 250 ml each of water. The organic phase is dried on sodium sulfate, and the solvent is evaporated to the dry state. The crude product is recrystallized from methyl-tert-butyl ether.

Yield: 60 g (77% of theory) of a colorless solid
Yield: 33.1 g (42% of theory) of a colorless solid
Elementary analysis:
Cld.: C 21.50 H 1.90 N 6.96
Fnd.: C 27.72 H 1.97 N 6.86 b) 2,4,6-Triiodo-5-({10-[1,4,7-tris-(benzyloxycarbonyl)-1,4,7,10-tetraazacyclododecanyl]}-acetyl)aminoisophthalic acid-N,N-bis-(3-aza-4-oxopentane-1,5-diyl-{10-[1,4,7-tris-(benzyloxycarbonyl)-1,4,7,10-tetraazacyclododecanyl]})amide 68.5 g (199.2 mmol) of 1,4,7-tris-(benzyloxycarbonyl)-1,4,7,10-tetrazacyclododecane (Delaney et al., *J. Chem. Soc. Perkin Trans.* 1991, 3329) is dissolved in 500 ml of acetonitrile and mixed with 33.5 g (238.4 mmol) of sodium carbonate. Then, while being stirred vigorously, 32 g (31.8 mmol) of N,N-bis-[2-(bromoacetylamino)ethyl]-5-[(bromoacetyl)amino]-2,4,6-triiodoisophthalic acid amide is added, and it is refluxed for 20 hours. Insoluble components are filtered out, it is evaporated to the dry state, and the residue is chromatographed on silica gel (mobile solvent: dichloromethane/methanol 20:1). The fractions that contain the product are combined and concentrated by evaporation.

Yield: 60.7 g (77% of theory) of a colorless solid
Elementary analysis:
Cld.: C 55.05 H 5.27 N 9.57 I 15.31
Fnd.: C 55.22 H 5.24 N 9.51 I 15.23 c) 2,4,6-Triiodo-5-[(1,4,7,10-tetraazacyclododecanyl)acetyl]aminoisophthalic acid-N,N-bis-[3-aza-4-oxopentane-1,5-diyl-(1,4,7,10-tetraazacyclododecanyl)]amide 60 g (24.1 mmol) of 2,4,6-triiodo-5-({10-[1,4,7-tris-(benzyloxycarbonyl)-1,4,7,10-tetraazacyclododecanyl]}acetyl)aminoisophthalic acid -N,N-bis-(3-aza-4-oxopentane-1,5-diyl-{10-[1,4,7-tris-(benzyloxycarbonyl)-1,4,7,10-tetraazacyclododecanyl]})amide is carefully mixed at 0-5° C. with 500 ml of HBr/AcOH (33%) and stirred for 3 hours at room temperature. Then, the reaction mixture is poured into 2500 ml of diethyl ether, the solid that accumulates in this case is suctioned off, and it is rewashed several times with diethyl ether. The residue is dissolved in 300 ml of water and 300 ml of dichloromethane while being stirred vigorously, and 32% NaOH solution is added until a pH of 10 is reached. The organic phase is separated, the aqueous phase is extracted three times with 150 ml each of dichloromethane, the combined organic phases are dried on magnesium sulfate, and it is evaporated to the dry state.

Yield: 29.4 g (95% of theory) of a colorless solid
Elementary analysis:
Cld.: C 39.41 H 5.99 N 18.60 I 29.75
Fnd.: C 39.65 H 6.04 N 18.55 I 29.63 d) 2,4,6-Triiodo-5-({10-[1,4,7-tris-(carboxymethyl)-1,4,7,10-tetraazacyclododecanyl]}acetyl)aminoisophthalic acid-N,N-bis-(3-aza-4-oxopentane-1,5-diyl-{10-[1,4,7-tris-(carboxymethyl)-1,4,7,10-tetraazacyclododecanyl]})amide 28 g (21.7 mmol) of 2,4,6-triiodo-5-[(1,4,7,10-tetraazacyclododecanyl)acetyl]aminoisophthalic acid-N,N-bis-[3-aza-4-oxopentane-1,5-diyl-(1,4,7,10-tetraazacyclododecanyl)]amide is dissolved in 300 ml of water, 31.3 g (332.3 mmol) of chloroacetic acid is added, and a pH of 9.5 is set at 60° C. with 32% NaOH. It is heated for 10 hours to 70° C., whereby the pH of the reaction mixture is continuously reset to 9.5. After cooling to room temperature, a pH of 1 is set with concentrated HCl, and the solution is concentrated by evaporation in a vacuum. The residue is absorptively precipitated with 200 ml of methanol, insoluble components are filtered out, and the filtrate is concentrated by evaporation. The residue is dissolved in 300 ml of water and added to an ion-exchange column (1200 ml, IR 120, H⁺-form). Then, it is washed with 5 l of water, and the acid eluate is concentrated by evaporation. The residue is dissolved in 150 ml of methanol and added in drops in 3000 ml of diethyl ether, the solid that accumulates in this case is suctioned off, rewashed several times with diethyl ether and dried in a vacuum.

Yield: 28.6 g (73% of theory) of a colorless solid
Elementary analysis:
Cld.: C 39.99 H 5.26 N 13.21 I 20.42
Fnd.: C 40.21 H 5.31 N 13.19 I 20.28 e) 2,4,6-Triiodo-5-({10-[1,4,7-tris-(carboxymethyl)-1,4,7,10-tetraazacyclododecanyl]}acetyl, Gd-complex)aminoisophthalic acid-N,N-bis-(3-aza-4-oxopentane-1,5-diyl-{10-[1,4,7-tris-(carboxymethyl)-1,4,7,10-tetraazacyclododecanyl, Gd-complex]})amide 12.4 g (6.9 mmol) of 2,4,6-triiodo-5-({10-[1,4,7-tris-(carboxymethyl)-1,4,7,10-tetraazacyclododecanyl]}acetyl)aminoisophthalic acid-N,N-bis-(3-aza-4-oxopentane-1,5-diyl-{10-[1,4,7-tris-(carboxymethyl)-1,4,7,10-tetraazacyclododecanyl]})amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 8.1 g (48% of theory) of a colorless solid
Water content (Karl-Fischer): 6.9%
Elementary analysis (relative to the anhydrous substance):
Cld.: C 32.81 H 3.78 N 10.51 I 16.81 Gd 20.83
Fnd.: C 32.99 H 3.81 N 10.49 I 16.75 Gd 20.69

Example 8 a) N,N-Bis-[2-tert-butoxycarbonylaminoacetyl-(2-aminoethyl)]-5-(methylamino)-2,4,6-triiodoisophthalic acid amide A solution of 10 g (16.4 mmol) of 2,4,6-triiodo-5-(methylamino)-isophthalic acid dichloride (EP 0033426, Sovak, 1/80 US) in 100 ml of tetrahydrofuran is added in drops to a solution of 7.82 g (36 mmol) of [(2-aminoethylcarbamoyl)methyl]carbamic acid-tert-butyl ester (Sobirov et al., *Russ. J. Bioorg. Chem.* (*Engl. Transl.*) 1994, 397) and 10 ml of triethylamine in 200 ml of tetrahydrofuran over 1 hour at room temperature, and stirring is continued for 14 hours. Insoluble components are filtered out, it is evaporated to the dry state, and the residue is chromatographed on silica gel (mobile solvent: ethyl acetate/hexane 1:1). The fractions that contain the product are combined and concentrated by evaporation.

Yield: 13.5 g (85% of theory) of a colorless solid
Elementary analysis:
Cld.: C 34.69 H 4.37 N 10.11 I 39.27
Fnd.: C 24.91 H 4.45 N 10.98 I 39.04 b) N,N-Bis-[2-(2-aminoacetylamino)ethyl]-5-(methylamino)-2,4,6-triiodoisophthalic acid amide 13 g (13.4 mmol) of N,N-bis-[2-tert-butoxycarbonylaminoacetyl-(2-aminoethyl)]-5-(methylamino)-2,4,6-triiodoisophthalic acid amide is carefully mixed at 0-5° C. with 100 ml of trifluoroacetic acid, and it is stirred for 3 hours at room temperature. Then, the reaction mixture is poured into 1500 ml of diethyl ether, the solid that accumulates in this case is suctioned off, and it is rewashed several times with diethyl ether. The residue is dissolved in 200 ml of water and 200 ml of dichloromethane while being stirred vigorously, and 32% NaOH solution is added until a pH of 10 is reached. The organic phase is separated, the aqueous phase is extracted three times with 100 ml each of dichloromethane, the combined organic phases are dried on magnesium sulfate and evaporated to the dry state.

Yield: 9.9 g (96% of theory) of a colorless solid
Elementary analysis:
Cld.: C 26.48 H 3.14 N 12.71 I 49.37
Fnd.: C 26.64 H 3.12 N 12.76 I 49.19 c) N,N-Bis-[2-(2-bromopropionylaminoacetylamino)ethyl]-5-[(2-bromopropionyl)methylamino]-2,4,6-triiodoisophthalic acid amide 57.8 g (75 mmol) of N,N-bis-[2-(2-aminoacetylamino)ethyl]-5-(methylamino)-2,4,6-triiodoisophthalic acid amide is dissolved in 500 ml of dimethylacetamide, and 75.5 g (350 mmol) of 2-bromopropionic acid bromide (Aldrich) is added in drops over 15 minutes at 0° C. Then, it is stirred for 20 hours at 40° C. The reaction mixture is poured into 4000 ml of ice water, the solid that accumulates is filtered off, dissolved in 800 ml of ethyl acetate and extracted three times with 250 ml each of water. The organic phase is dried on sodium sulfate, and the solvent is evaporated to the dry state. The crude product is recrystallized from methyl-tert-butyl ether.

Yield: 54.8 g (62% of theory) of a colorless solid
Elementary analysis:
Cld.: C 26.55 H 2.83 N 8.34
Fnd.: C 26.77 H 2.86 N 8.21 d) 2,4,6-Triiodo-5-(2-{10-[1,4,7-tris-(benzyloxycarbonyl)-1,4,7,10-tetraazacyclododecanyl]}-propionyl)methylaminoisophthalic acid-N,N-bis-(3,6-diaza-4,7-dioxo-8-methyloctane-1,5-diyl-{10-[1,4,7-tris-(benzyloxycarbonyl)-1,4,7,10-tetraazacyclododecanyl]})amide 98.9 g (172.1 mmol) of 1,4,7-tris-(benzyloxycarbonyl)-1,4,7,10-tetraazacyclododecane (Delaney et al., *J. Chem. Soc. Perkin Trans.* 1991, 3329) is dissolved in 800 ml of acetonitrile and mixed with 47.6 g (344.3 mmol) of sodium carbonate. Then, 54 g (45.9 mmol) of N,N-bis-[2-(2-bromopropionylamino-acetylamino)ethyl)-5-[(2-bromopropionyl)methylamino]-2,4,6-triiodoisophthalic acid amide is added while being stirred vigorously, and it is refluxed for 20 hours. Insoluble components are filtered out, evaporated to the dry state, and the residue is chromatographed on silica gel (mobile solvent: dichloromethane/methanol 20:1). The fractions that contain the product are combined and concentrated by evaporation.

Yield: 52.6 g (43% of theory) of a colorless solid
Elementary analysis:
Cld.: C 55.14 H 5.46 N 10.01 I 14.33
Fnd.: C 55.27 H 5.44 N 9.98 I 14.21 e) 2,4,6-Triiodo-5-[2-(1,4,7,10-tetraazacyclododecanyl)propionyl]methylaminoisophthalic acid-N,N-bis-[3,6-diaza-4,7-dioxo-8-methyloctane-1,5-diyl-(1,4,7,10-tetraazacyclododecanyl)]amide 51.5 g (19.4 mmol) of 2,4,6-triiodo-5-(2-{10-[1,4,7-tris-(benzyloxycarbonyl)-1,4,7,10-tetraazacyclododecanyl]}propionyl)methylaminoisophthalic acid-N,N-bis-(3,6-diaza-4,7-dioxo-8-methyloctane-1,5-diyl-{10-[1,4,7-tris-(benzyloxycarbonyl)-1,4,7,10-tetraazacyclododecanyl]}) amide is carefully mixed at 0-5° C. with 500 ml of HBr/AcOH (33%) and stirred for 3 hours at room temperature. Then, the reaction mixture is poured into 2500 ml of diethyl ether, the solid that accumulates in this case is suctioned off, and it is rewashed several times with diethyl ether. The residue is dissolved in 300 ml of water and 300 ml of dichloromethane while being stirred vigorously, and 32% NaOH solution is added until a pH of 10 is reached. The organic phase is separated, the aqueous phase is extracted three times with 150 ml each of dichloromethane, the combined organic phases are dried on magnesium sulfate and evaporated to the dry state.

Yield: 26.7 g (95% of theory) of a colorless solid
Elementary analysis:
Cld.: C 41.41 H 6.26 N 18.35 I 26.25
Fnd.: C 41.57 H 6.28 N 17.29 I 26.09 f) 2,4,6-Triiodo-5-(2-{10-[1,4,7-tris-(carboxymethyl)-1,4,7,10-tetraazacyclododecanyl]}propionyl)methylaminoisophthalic acid-N,N-bis-(3,6-diaza-4,7-dioxo-8-methyloctane-1,5-diyl-{10-[1,4,7-tris-(carboxymethyl)-1,4,7,10-tetraazacyclododecanyl]})amide 25.8 g (17.8 mmol) of 2,4,6-triiodo-5-[2-(1,4,7,10-tetraazacyclododecanyl)-propionyl]methylaminoisophthalic acid-N,N-bis-[3,6-diaza-4,7-dioxo-8-methyloctane-1,5-diyl-(1,4,7,10-tetraazacyclododecanyl)]amide is dissolved in 200 ml of water, 25.7 g (272.7 mmol) of chloroacetic acid is added, and it is set at a pH of 9.5 with 32% NaOH at 60° C. It is heated for 10 hours to 70° C., whereby the pH of the reaction mixture is continuously reset to 9.5. After cooling to room temperature, a pH of 1 is set with concentrated HCl, and the solution is concentrated by evaporation in a vacuum. The residue is absorptively precipitated with 300 ml of methanol, insoluble components are filtered out, and the filtrate is concentrated by evaporation. The residue is dissolved in 200 ml of water and added to an ion-exchange column (1200 ml, IR 120, H+-form). Then, it is washed with 5 l of water, and the acid eluate is concentrated by evaporation. The residue is dissolved in 150 ml of methanol and added in drops to 2500 ml of diethyl ether, the solid that accumulates in this case is suctioned off, rewashed several times with diethyl ether, and dried in a vacuum.

Yield: 23.2 g (66% of theory) of a colorless solid
Elementary analysis:
Cld.: C41.41 H5.52 N 13.49 I 19.30
Fnd.: C 41.62 H 5.53 N 13.37 I 19.13 g) 2,4,6-Triiodo-5-(2-{10-[1,4,7-tris-(carboxymethyl)-1,4,7,10-tetraazacyclododecanyl]}propionyl, Gd-complex)methylaminoisophthalic acid-N,N-bis-(3,6-diaza-4,7-dioxo-8-methyloctane-1,5-diyl-{10-[1,4,7-tris-(carboxymethyl)-1,4,7,10-tetraazacyclododecanyl, Gd-complex]})amide 13.6 g (6.9 mmol) of 2,4,6-triiodo-5-(2-{10-[1,4,7-tris-(carboxymethyl)-1,4,7,10-tetraazacyclododecanyl]}propionyl)methylaminoisophthalic acid-N,N-bis-(3,6-diaza-4,7-dioxo-8-methyloctane-1,5-diyl-{10-[1,4,7-tris-(carboxymethyl)-1,4,7,10-tetraazacyclododecanyl]})amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 11.1 g (61% of theory) of a colorless solid
Water content (Karl-Fischer): 7.5%
Elementary analysis (relative to the anhydrous substance):
Cld.: C 33.54 H 4.10 N 10.93 I 15.63 Gd 19.37
Fnd.: C 33.71 H 4.08 N 10.88 I 15.49 Gd 19.21

Example 9

Comparison Example

In comparison to the compounds according to the invention, compound 3 from Example 3 and compound 4 from Example 4, disclosed in the closest prior art from U.S. Pat. No. 5,660,814, are 5) ionic and thus have an osmolality that is higher by a factor of 2 in comparison to the neutral compounds according to the invention, which is especially negative at high doses,
6) the latter are significantly more lipophilic than the compounds according to the invention (Note in column 5/line 29 of U.S. Pat. No. 5,660,814, the compounds from the prior art can be used as liver contrast media),
7) substances 3 and 4 of U.S. Pat. No. 5,660,814 are significantly more toxic than the compounds according to the invention (see $LD_{50}$ as well as distribution coefficient) and
8) the relaxivity for the MR imaging is thus lower.

|  | Example 1 | Example 5 | Example 7 | Example 8 | Example 3 from U.S. Pat. No. 5,660,814 | Example 4 from U.S. Pat. No. 5,660,814A |
|---|---|---|---|---|---|---|
| Osmolality 200 mg (I + Gd)/ml [mosmol/l] | 358 | 371 | 334 | 346 | ~750 as Na-salt | ~730 as Na-salt |

|  | Example 1 | Example 5 | Example 7 | Example 8 | Example 3 from U.S. Pat. No. 5,660,814 | Example 4 from U.S. Pat. No. 5,660,814A |
|---|---|---|---|---|---|---|
| BuOH/H$_2$O Distribution Coefficient | 0.00005 | 0.00006 | 0.00005 | 0.00005 | 0.007 | 0.01 |
| Relaxivity T1 in H$_2$O | 9.8 | 10.1 | 10.3 | 10.0 | 6.3 | 7.2 |
| LD$_{50}$ (Mouse) | >12.0 g(I + Gd)/ kg | >12.0 g(I + Gd)/ kg | >12.0 g(I + Gd)/ kg | >12.0 g(I + Gd)/ kg | >2.0 g(I + Gd)/ kg | >2.0 g(I + Gd)/ kg |

The entire disclosures of all applications, patents and publications, cited herein and of corresponding German application No. 102004023093.5, filed May 5, 2004, and U.S. Provisional Application Ser. No. 60/574,713, filed May 27, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A metal complex of formula (I)

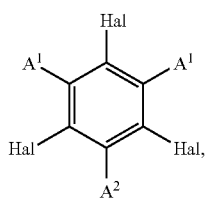

(I)

in which
Hal stands for bromine or iodine,
A$^1$ stands for the radical —CONR$^1$—(CH$_2$)$_n$—NR$^2$—(CO—CHZ$^1$—NH)$_m$—CO—CHZ$^2$—K,
A$^2$ stands for the radical —NR$^1$—CO—CHZ$^2$—K,
R$^1$ and R$^2$ are, independently of one another, a hydrogen atom, a C$_1$-C$_2$-alkyl group or a monohydroxy-C$_1$-C$_2$-alkyl group,
Z$^1$ and Z$^2$ are, independently of one another, a hydrogen atom or a methyl group,
n is the number 2-4,
m is the number 0 or 1, and
K stands for

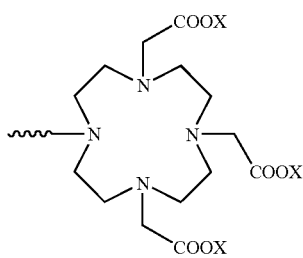

(I$_A$)

wherein X is a hydrogen atom or a metal ion equivalent of atomic numbers 20-29, 39, 42, 44 or 57-83, provided that at least two X stand for metal ion equivalents and optionally present free carboxy groups optionally are present as salts of organic and/or inorganic bases or amino acids or amino acid amides.

2. A metal complex according to claim 1, wherein A$^1$ stands for

—CONH(CH$_2$)$_{2,3}$NHCOCH$_2$NHCOCH(CH$_3$)—K,

—CONH(CH$_2$)$_{2,3}$NHCOCH$_2$NHCOCH$_2$—K,

—CONH(CH$_2$)$_{2,3}$NHCOCH$_2$—K,

—CONH(CH$_2$)$_{2,3}$NHCOCH(CH$_3$)—K, or

—CON(CH$_2$CH$_2$OH(CH$_2$)$_2$NHCOCH$_2$—K.

3. A metal complex according to claim 1, wherein A$^2$ stands for

—NHCOCH(CH$_3$)—K,

—NHCOCH$_2$—K,

—N(CH$_3$)COCH$_2$—K,

—N(CH$_3$)COCH(CH)$_3$—K,

—N(CH$_2$CH$_2$OH)COCH$_2$—K, or

—N(CH$_2$CH$_2$OH)COCH(CH$_3$)—K.

4. A metal complex according to claim 1, wherein X stands for a metal ion equivalent of atomic numbers 21-29, 42, 44, or 58-70.

5. A metal complex according to claim 1, wherein X stands for a metal ion equivalent of ions gadolinium(III), dysprosium(III), europium(III), iron(III) or manganese(II).

6. A pharmaceutical composition comprising at least one metal complex according to claim 1, and a galenically acceptabe carrier.

7. A method for x-ray diagnosis, comprising administering to a subject an effective amount of a metal complex according to claim 1 and x-ray imaging said subject.

8. A method for MRT diagnosis, comprising administering to a subject an effective amount of a metal complex according to claim 1 and MRT imaging said subject.

9. A pharmaceutical composition according to claim 6, which contains a metal complex according to claim 1 in a molar ratio of 2000:1 to 1:1.

10. Pharmaceutical agents according to claim 6, wherein the metal complex is dissolved or suspended in water or is in a physiologically salt solution at a concentration of 0.001 to 1 mol/l.

11. A method for x-ray or MR diagnosis of cerebral infarction, a tumor of the liver, a space-occupying process in the liver, a tumor of the abdomen, a tumor of the kidney, or the muscle-skeleton system, or and for the visualization of a blood vessel after intraarterial injection or intravenous injection, comprising administering to a subject an effective amount of a metal complex according to claim 1 and x-ray or MR imaging said subject.

12. A process for preparing a metal complex according to claim 1, comprising reacting a triiodoaromatic compound or a tribromoaromatic compound of formula II

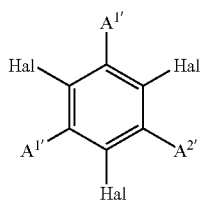

(II)

with a compound of formula III

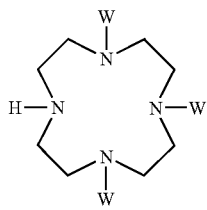

(III)

in which
Hal stands for bromine or iodine,
W stands for a protective group or a —CH$_2$COOX' group,
X' has the meaning of X in the compound of formula (I) or is protective group,
A$^{1'}$ is —CO—NR$^1$—(CH$_2$)$_n$—NR$^2$—(CO—CHZ$^1$—NH)$_m$—CO—CHZ$^2$—Hal',
A$^{2'}$ is —NR$^1$—CO—CHZ$^2$—Hal',
Hal' is chlorine or bromine,
and R$^1$, R$^2$, Z$^1$, Z$^2$, m and n are as defined in the compound of formula (I),
and then optionally removing protective group W and introducing the radical CH$_2$COOX, or removing the protective group that optionally stands for X' and then reacting with a metal oxide or metal salt of an element of one of the atomic numbers 20-29, 39, 42, 44 and 57-83.

13. A process for preparing a pharmaceutical composition according to claim 6, wherein the at least one metal complex is dissolved or suspended in water or in a physiologically acceptable salt solution.

14. A pharmaceutical composition according to claim 6, which is suitable for enteral or parenteral administration.

15. A pharmaceutical composition according to claim 6, which contains a metal complex according to claim 1 in a molar ratio of 49:1 to 4:1.

16. A metal complex according to claim 1, wherein Hal is iodine, R$^1$ and R$^2$ are hydrogen or methyl, m is 0 and n is 2.

17. A method for x-ray diagnosis, comprising administering to a subject an effective amount of a metal complex according to claim 16 and x-ray imaging said subject.

18. A method for MRT diagnosis, comprising administering to a subject an effective amount of a metal complex according to claim 16 and MRT imaging said subject.

19. A method for x-ray or MR diagnosis of cerebral infarction, a tumor of the liver, a space-occupying process in the liver, a tumor of the abdomen, a tumor of the kidney, or the muscle-skeleton system, or and for the visualization of a blood vessel after intraarterial injection or intravenous injection, comprising administering to a subject an effective amount of a metal complex according to claim 16 and x-ray or MR imaging said subject.

20. A metal complex according to claim 16, wherein
A$^1$ stands for

—CONH(CH$_2$)$_{2,3}$NHCOCH$_2$NHCOCH(CH$_3$)—K,

—CONH(CH$_2$)$_{2,3}$NHCOCH$_2$NHCOCH$_2$—K,

—CONH(CH$_2$)$_{2,3}$NHCOCH$_2$—K,

—CONH(CH$_2$)$_{2,3}$NHCOCH(CH$_3$)—K, or

—CON(CH$_2$CH$_2$OH(CH$_2$)$_2$NHCOCH$_2$—K, and
A$^2$ stands for

—NHCOCH(CH$_3$)—K,

—NHCOCH$_2$—K,

—N(CH$_3$)COCH$_2$—K,

—N(CH$_3$)COCH(CH$_3$)—K,

—N(CH$_2$CH$_2$OH)COCH$_2$—K, or

—N(CH$_2$CH$_2$OH)COCH(CH$_3$)—K.

* * * * *